(12) United States Patent
Quinn et al.

(10) Patent No.: US 7,862,514 B2
(45) Date of Patent: Jan. 4, 2011

(54) BLOOD PRESSURE MEASUREMENT

(75) Inventors: David E. Quinn, Auburn, NY (US); Matthew J. Kinsley, Liverpool, NY (US); Tyson B. Whitaker, Arden, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1354 days.

(21) Appl. No.: 11/347,889

(22) Filed: Feb. 6, 2006

(65) Prior Publication Data

US 2007/0185401 A1    Aug. 9, 2007

(51) Int. Cl.
*A61B 5/02* (2006.01)

(52) U.S. Cl. .................. 600/490; 600/485; 600/500

(58) Field of Classification Search ............ None
See application file for complete search history.

(56) References Cited

U.S. PATENT DOCUMENTS

| | | | |
|---|---|---|---|
| 4,261,368 A | 4/1981 | Danna et al. | |
| 4,408,599 A | 10/1983 | Mummert | |
| 4,458,690 A | 7/1984 | O'Connor et al. | |
| 4,461,266 A | 7/1984 | Hood, Jr. et al. | |
| 4,718,427 A | 1/1988 | Russell | |
| 5,235,973 A | 8/1993 | Levinson | |
| 5,447,161 A | 9/1995 | Blazek et al. | |
| 5,570,694 A * | 11/1996 | Rometsch | 600/493 |
| 5,632,278 A | 5/1997 | Rometsch | |
| 6,450,966 B1 | 9/2002 | Hanna | |
| 2002/0087087 A1 | 7/2002 | Oka et al. | |
| 2003/0092999 A1 | 5/2003 | Goto et al. | |
| 2004/0127801 A1 | 7/2004 | Takahashi et al. | |
| 2004/0147848 A1 | 7/2004 | Shirasaki et al. | |
| 2004/0220482 A1 | 11/2004 | Booth | |
| 2004/0254480 A1 | 12/2004 | Band et al. | |
| 2005/0033188 A1 | 2/2005 | Whitaker et al. | |
| 2005/0245832 A1 | 11/2005 | Takahashi et al. | |

FOREIGN PATENT DOCUMENTS

EP     0775465     5/1997

OTHER PUBLICATIONS

European Search Report for EP Application No. 07710296.0; mailed Dec. 17, 2009; 5 pages.

* cited by examiner

*Primary Examiner*—Charles A Marmor, II
*Assistant Examiner*—Christian Jang
(74) *Attorney, Agent, or Firm*—Roger P. Bonenfant

(57) ABSTRACT

The diastolic blood pressure and a systolic blood pressure of a vertebrate are measured using an inflatable pressure cuff disposed about a limb of the vertebrate and connected to an inflation device through a single conduit. A pressure sensor is pneumatically connected to the cuff through the same common conduit. The sensed pressures at the diastolic and systolic points are corrected for a pressure differential associated with the flow of an inflation fluid through the common conduit. The sensed pressures at the diastolic point and the systolic point may be measured during inflation of the cuff or during controlled deflation of the cuff.

34 Claims, 5 Drawing Sheets

BLOOD PRESSURE MEASUREMENT

CROSS-REFERENCE TO RELATED APPLICATIONS

This application is related to co-pending U.S. patent application Ser. No. 10/619,380, filed Jul. 14, 2003, entitled "Motion Management in a Fast Blood Pressure Measurement Device," published Feb. 10, 2005, as Patent Application Publication No. US2005/0033188A1, and subject to assignment to the common assignee of the present application, which application is incorporated herein by reference in its entirety. This application is also related to co-pending U.S. patent application Ser. No. 11/032,625, filed Jan. 10, 2005, entitled "A Portable Vital Signs Measurement Instrument and Method of Use Thereof", and subject to assignment to the common assignee of the present application, which application is incorporated herein by reference in its entirety.

BACKGROUND OF THE INVENTION

This invention relates generally to the non-invasive measurement of blood pressure and, more particularly, to the measurement of blood pressure via an automated blood pressure apparatus.

The measurement of blood pressure is a common procedure used in hospitals, clinics and physicians' offices as a tool to assist in diagnosis of illness and monitoring of sick patients, as well as an indicator of the general status of a person's health. In standard non-invasive blood pressure measurement practice, blood pressure is measured using an inflatable sleeve, commonly referred to as a cuff, to measure arterial blood pressure. The cuff, which is adapted to fit around a limb over an artery of a patient, typically around the patient's upper arm over the brachial artery, includes an interior chamber adapted to be inflated with air to provide pressure on the artery.

Electronic blood pressure measurement devices for automatically inflating the cuff and automatically sensing the blood pressure either during inflation of the cuff or during deflation of the cuff are well-known in the art. In such devices, a motor driven pump is operatively connected to the interior chamber of the cuff by means of a tube, often referred to as a lumen. Upon activation of the pump motor, air is pumped by the pump through the tube to inflate the interior chamber of the cuff to a pressure sufficient to stop the blood flow through the artery. A bleed valve is also operatively connected in fluid communication with the interior chamber to permit depressuring of the interior chamber when it is desired to deflate the cuff, either step-wise or rapidly, as desired. Generally, a pressure sensing device, typically a pressure transducer, is operatively connected in fluid communication with the interior chamber of the cuff to directly sense the pressure within the interior chamber of the cuff.

Automated blood pressure measurement devices commonly employ either an ausculatory technique or an oscillometric technique to detect when the systolic blood pressure, which corresponds to the cessation of blood flow through the artery, is reached, and when the diastolic blood pressures, which corresponds to unrestricted blood flow through the artery, is reached. In a conventional ausculatory method, a sound sensing device, commonly a microphone, is provided in operative association with the cuff to listen for pulsating sounds, known as Korotkoff sounds, associated with the flow of blood through an artery under pressure. In a conventional oscillometric approach, one or more pressure sensing devices, for example pressure transducers, are provided in operative association with the cuff to detect small oscillatory pressures that occur within the cuff as the result of the pulsating characteristic of blood flow through the artery.

Electronic circuitry, including a central processing unit, is provided that processes the signals from the cuff pressure sensor, and, if present, the microphone or additional pressure sensors, and determines the systolic and diastolic blood pressures. Typically, a digital display is also provided for displaying the systolic and diastolic blood pressures. The signals indicative of the systolic and diastolic blood pressure measurements may be transmitted to an external device, such as a laptop or a patient monitor, for display and/or data recording.

Automated blood measurement devices may be either two-lumen or single lumen devices. In a two-lumen apparatus, the first lumen provides a conduit connecting the inflation chamber of the cuff in fluid communication with the pump and the second lumen provides a conduit connecting the inflation chamber of the cuff in fluid communication with a pressure transducer, or other pressure sensing device. Therefore, the chamber is inflated during the inflation period by the pump passing air flow through the first lumen, while the pressure within the cuff is monitored independently through a static second lumen, unaffected by the flow of air through the first lumen. In a single lumen device, however, the inflation chamber of the cuff is connected in fluid communication with both the pump and the pressure sensor through the conduit of single lumen. Consequently, on a single lumen device, the pressure sensed by the pressure sensor will be impacted by the pressure losses experienced by the air flowing through the first lumen. Therefore, at any given instant in the inflation process, the pressure sensed by the pressure sensor will be greater than the actual cuff pressure by an amount equal to the sum of the pressure losses experienced by the air being pumped through the first lumen.

The overall pressure loss encountered in a single lumen may attributed to a number of factors including the amount of airflow (i.e. the air flow rate), the resistance to flow through the tube itself, which varies dependent upon tube length and cross-sectional flow area, and the pressure drop through the connectors at the respective ends of the tube, with the air flow rate being the dominant determinant of pressure loss. The amount of air flow required to maintain a consistent pressure rise rate during the inflation of the cuff is variable and dependent upon a number of factors, including, for example, pump drive voltage, pump efficiency, cuff size, tightness of the cuff wrap about the patient's limb, limb stiffness, and cuff pressure. Given the number and complexity of these variables, it is not practical to attempt to calculate the actual pressure loss at a given point in the inflation process. Therefore, automated apparatus designed to measure the systolic and diastolic blood pressures during the inflation process, rather than during a step deflation process initiated only after full inflation of the cuff, use a two-lumen configuration. However, due to the convenience of and the patient comfort associated with the "inflation BP" technique, it would be desirable to have a method of accurately correcting the sensed cuff pressure to enable use of the "inflation BP" technique on a single-lumen blood pressure measurement apparatus. The accuracy standard for BP measurement established by the Association for the Advancement of Medical Instrumentation is +/− 3 millimeters Hg (three millimeters Mercury).

A detailed discussion and description of the operation of an exemplary embodiment of an electronic apparatus for the non-invasive measurement of blood pressure is presented in the aforementioned U.S. Patent Application Publication No. US2005/0033188A1.

U.S. Pat. No. 5,632,278 discloses a device for automatically measuring blood pressure using a sphygmomanometer cuff connected to a pressure generator and a pressure sensor via a common tube wherein the blood pressure measurements are made during a controlled deflation of the cuff.

U.S. Patent Application Publication No. US2004/0127801A1 discloses a noninvasive sphygmomanometer wherein blood pressure measurements, sensed during slow deflation of the sphygmomanometer cuff, are subsequently corrected based on a value of the arm circumference length calculated during the cuff inflation process based on a relationship between a pressure in the bladder of the cuff and the measured discharge amount of the pressure pump inflating the bladder.

European Patent Application No. EP0775465A1 discloses an automatic sphygmomanometer wherein if a first blood value that is determined while a pressure of the cuff is slowly increased is adjudged abnormal, a second blood pressure value is determined while the cuff pressure is decreased.

SUMMARY OF THE INVENTION

It is a general object of the present invention to provide a method of measuring diastolic and systolic blood pressures using a blood pressure cuff inflated through a common lumen in pneumatic communication with a pressure sensor.

It is an object of an aspect of the invention to provide a method for correcting sensed pressure measurements in a single lumen blood pressure measurement apparatus for pressure losses associated with the flow of an inflation fluid through the single lumen.

It is an object of one aspect of the present invention to provide a method of measuring diastolic and systolic blood pressures during the process of inflating a blood pressure cuff inflated through a common lumen in pneumatic communication with a pressure sensor.

It is an object of one aspect of the present invention to provide a method of measuring diastolic and systolic blood pressures during the process of deflating a blood pressure cuff inflated through a common lumen in pneumatic communication with a pressure sensor.

A method is provided for determining diastolic and systolic blood pressures using an inflatable pressure cuff disposed about a vertebrate's limb and connected to a blood pressure measurement apparatus through a single conduit having a distal end in fluid communication with the inflatable cuff and a proximal end in fluid communication with an inflation device and also in pneumatic communication with a pressure sensor. The cuff is inflated by passing a flow of an inflation fluid, typically air, through the conduit. The fluid pressure is sensed at the proximal end of the conduit by the pressure sensor at the diastolic and systolic points. A pressure differential exists between the cuff and the pressure sensor due to the pressure losses experienced by the flow of the inflation fluid through the conduit. The pressured differential associated with the flow of the inflation fluid through the common conduit is determined at the diastolic point and at the systolic point, and the sensed pressures at the diastolic and systolic points are corrected for the pressure differential between the sensed pressures and the respective actual cuff pressures.

In an embodiment of the method of the invention, correcting the sensed pressures at the diastolic and systolic points includes the steps of stopping the cuff inflation process; after a time delay measuring the pressure differential existing over the conduit between the cuff and the pressure sensor; and calculating the respective pressure differentials associated with the sensed pressures at the diastolic and systolic points as a function of the measured pressure differential. In a particular embodiment, the inflation process is terminated at a pressure exceeding the systolic point, the fluid pressure is sensed immediately prior to termination of the cuff inflation process and at the end of a time delay following the termination of the cuff inflation sufficient for fluid pressure within the cuff and in the conduit to equalize, and the fluid pressure after the time delay is subtracted from the fluid pressure immediately prior to termination of the cuff inflation process to provide the measured pressure differential existing over the conduit at termination of the cuff inflation process. In an embodiment, the time delay is approximately one second.

The pressure differential associated with the sensed pressure at the diastolic point may be calculated as a function of the measured pressure differential using the relationship:

$$\Delta P_{DIA} = (F_{DIA}/F_M)\Delta P_M, \text{ where:}$$

$\Delta P_{DIA}$ is the pressure differential between the pressure sensed at the sensor and the pressure within the cuff when the diastolic point is reached;

$\Delta P_M$ is the actual measured pressure differential at the sensor at the measurement point;

$F_{DIA}$ is the air flow rate through the conduit at the diastolic point; and $F_M$ is the air flow rate through the conduit at the measurement point.

The pressure differential associated with the sensed pressure at the systolic point may be calculated as a function of the measured pressure differential using the relationship:

$$\Delta P_{SYS} = (F_{SYS}/F_M)\Delta P_M, \text{ where:}$$

$\Delta P_{SYS}$ is the pressure differential between the pressure sensed at the sensor and the pressure within the cuff when the systolic point is reached;

$\Delta P_M$ is the actual measured pressure differential at the sensor at the measurement point;

$F_{SYS}$ is the air flow rate through the conduit at the systolic point; and $F_M$ is the air flow rate through the conduit at the measurement point.

With respect to correction of the blood pressure measurements taken during the cuff inflation process, the air flow rates used in calculating $\Delta P_{SYS}$ and $\Delta P_{DIA}$ based on $\Delta P_M$ are measured at the respective points during the cuff inflation process wherein the air flow is flowing through the conduit to the cuff. With respect to correction of the blood pressure measurements taken during the cuff deflation process, the air flow rates used in calculating $\Delta P_{SYS}$ and $\Delta P_{DIA}$ based on $\Delta P_M$ are measured at the respective points during the cuff deflation process wherein the air flow is flowing through the conduit from the cuff.

In an embodiment of the invention wherein the diastolic and systolic blood pressures are sensed during the inflation of the cuff, the true diastolic blood pressure is determined by subtracting the diastolic pressure differential from the sensed pressure at the diastolic point and the true systolic blood pressure is determined by subtracting the systolic pressure differential from the sensed pressure at the systolic point. In an embodiment of the invention wherein the diastolic and systolic blood pressures are sensed during the deflation of the cuff, the true diastolic blood pressure is determined by adding the diastolic pressure differential from the sensed pressure at the diastolic point and the true systolic blood pressure is determined by adding the systolic pressure differential from the sensed pressure at the systolic point.

BRIEF DESCRIPTION OF THE DRAWINGS

For a further understanding of these and objects of the invention, reference will be made to the following detailed description of the invention which is to be read in connection with the accompanying drawing, where.

DETAILED DESCRIPTION OF THE INVENTION

Figure 1:
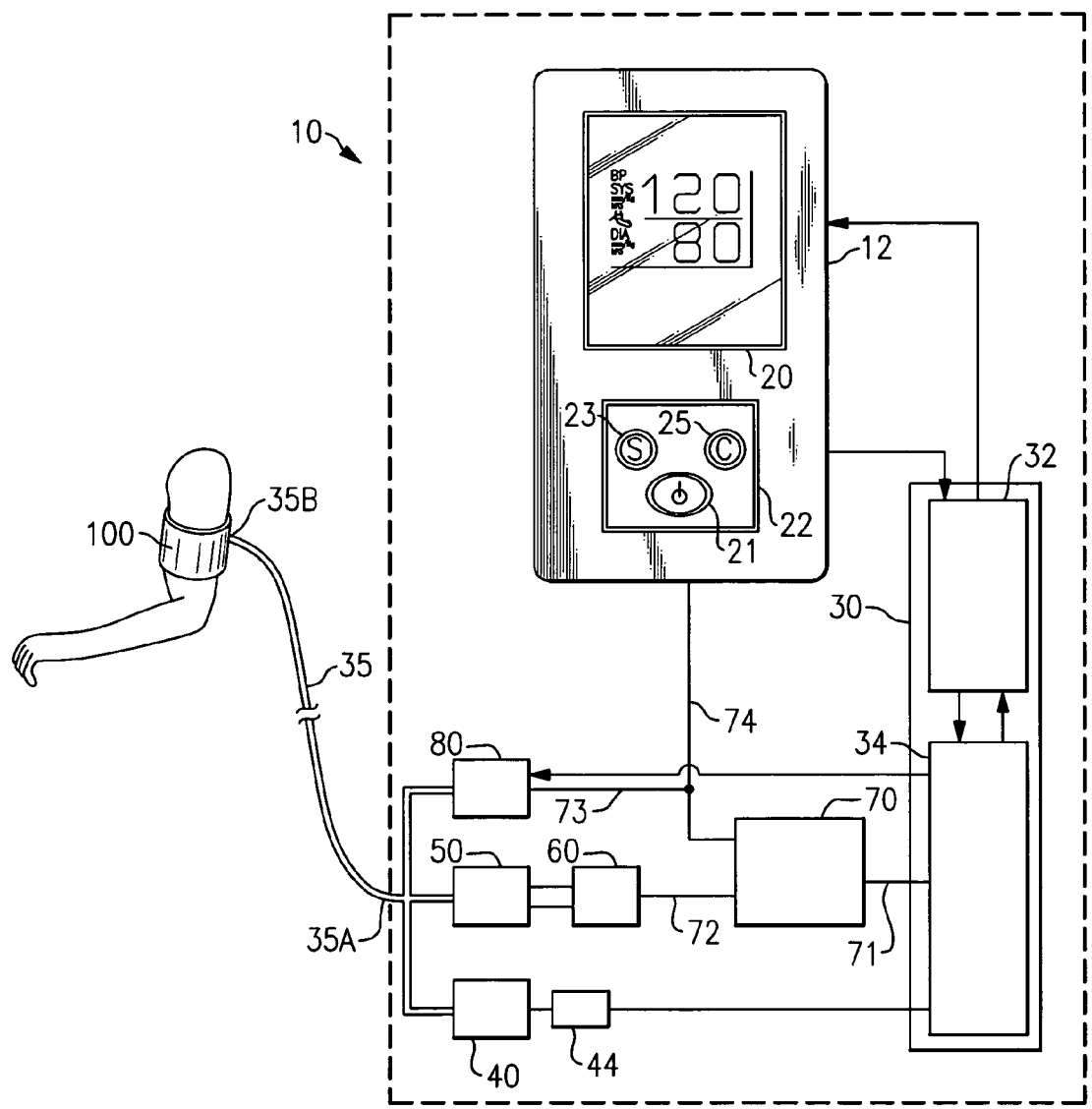
FIG. 1 is a schematic diagram of an embodiment of a blood pressure measurement apparatus in accordance with the invention.

The present invention will be described herein with reference to an exemplary embodiment of a modular blood pressure measurement apparatus 10 depicted in FIG. 1. In the depicted embodiment, the blood pressure measurement apparatus 10 includes a display 20 and a user interface 22 operatively connected to a controller 30 that includes a central processing unit, "CPU", 32 and non-invasive blood pressure module, "NIBP", 34. The blood pressure measurement apparatus 10 further includes a pressure sensor 40, an air pump 50, a direct current motor 60, a power supply 70, such as rechargeable battery power pack, and a vent valve 80. The power supply 70 supplies power to the controller 30 through line 71, to the DC motor 60 through line 72, to the vent valve 80 through line 73 and to the display 20 and user interface 22 through line 74. The pressure sensor 40, the pump 50 and vent valve 80 are coupled in pneumatic communication in a conventional manner via a common flexible conduit 35 to a blood pressure measurement cuff 100 applied to a limb of a vertebrate. The conduit 35, also commonly referred to as a lumen, may be a rubber tube or a conduit of other suitable material. The cuff 100 may be any conventional type of blood pressure measurement cuff, such as various "monitor" style cuffs available from Welch Allyn, Inc., headquartered in Skaneateles, N.Y., in sizes for thigh, large adult, adult, small adult, child, small child, infant and neonate.

The pressure sensor 40 is housed within the apparatus 10 in operative association with the NIBP module 34 and is in direct pneumatic communication with the proximal end 35A of the conduit 35 for monitoring the pressure within the interior inflation chamber of the cuff. The pressure sensor 40 also detects minute changes in cuff pressure due to blood flow in the patient's artery, as the cuff inflates. A sensor electronics module 44 is provided in operative association with the pressure sensor 40 for receiving the sensed pressure reading from the pressure sensor 40, converting the reading to an electrical signal indicative of the sensed pressure, and transmitting that digital signal indicative of the sensed pressure to the NIBP module 34 or, if desired, directly to the microcontroller. The pressure sensor 40 may comprise a conventional pressure transducer, in which case the sensor electronics module 44 will include an analog-to-digital signal conversion routine.

The display 20 includes a region for displaying information relating to a blood pressure measurement including the systolic blood pressure (SYS) and the diastolic blood pressure (DIA) measurements in either millimeters of Mercury ("mmHg") or Pascals ("kPa"). The display 20 may also be configured to display mean pressure, heart rate, or other information. Both the systolic and diastolic blood pressures are displayed as a numeric two or three digit number. For purposes of illustration, the systolic and diastolic blood pressures are shown in FIG. 1 as 120 mmHg and 80 mmHg, respectively. The display 20 may be a LCD display, a LED display, or any other suitable display device.

The user interface 22 may include, for example, a plurality of input keys 21, 23 and 25. Key 21 is an on/off switch for selectively powering the apparatus 10 on and off. Key 23 is a start switch for selectively initiating a blood pressure measurement procedure and key 25 is stop switch for selectively canceling a blood pressure measurement procedure.

The controller 30 includes a control circuit including the CPU 32 and the NIBP module 34 on a printed circuit board supported within the housing (not shown) of the apparatus 10. The CPU 32, for example a microprocessor, interacts with the display 20, the input keys 21, 23 and 25, and the NIPB module 34. The NIBP module 34, which may be a software module incorporated into the microprocessor 32 or may comprise a separate microprocessor coupled in communication with the microprocessor 32, controls operation of the pump 50, the DC motor 60 and the vent valve 80. The pump 50, which may be a rotary positive displacement pump or other type of inflation pump, when the pump motor 60 is activated in response to a command signal from the controller 30, pumps an inflation fluid, typically air, through the single conduit 35 to inflate the blood pressure cuff 100. The vent valve 80, which is also pneumatically coupled to the blood pressure cuff 100 through the conduit 35, provides for selective venting of air from the cuff 100 to deflate the cuff in response to a command signal from the controller 30.

As in conventional practice, to initiate a blood pressure measurement procedure, the user depresses the on/off switch key 21 to power up the various components of the blood pressure measurement apparatus 10. With the blood pressure measurement cuff 100 in place on the patient, the user depresses the start key 23 to initiate the blood pressure measurement procedure. In response, the microprocessor 32 activates the NIBP module 34 and a command signal is sent to activate the motor 60 to drive the pump 50 to inflate the cuff 100. During the cuff inflation process, the cuff pressure is continuously monitored by the pressure sensor 40 and signals indicative of the cuff pressure transmitted by the sensor electronics module 44 to the NIBP module 34. Thus, the NIBP module 34 knows the pressure sensed by the pressure sensor 40 at any time in the cuff inflation process. Further, via conventional oscillometric techniques well-known to those of ordinary skill in the art, the NIBP module 34 detects the diastolic and systolic pressure points. It is to be understood, however, that the method of the invention is not limited to any particular method for detecting the diastolic and systolic points, and that other techniques known in the art, rather than oscillometric techniques, may be used for detecting the diastolic and systolic points. For example, the apparatus 10 may be equipped with a sound sensing device in operative association with the cuff 100 to listen for Korotkoff sounds for detecting the diastolic and systolic points in accord with conventional ausculatory methods well known to persons having ordinary skill in the art.

The inflation chamber of the inflatable cuff 100, which is connected in pneumatic communication with the distal end 35B of the conduit 35, is connected by the single conduit 35 with the pump 50 and the pressure sensor 40, both of which are connected in pneumatic communication with the proximal end 35A of the conduit 35. During the period of inflating the cuff to a pressure above the systolic point, a flow of air passes through the conduit 35 from the pump 50 to the cuff 100. As the air flow passes through the conduit 35, pressure losses occur which result in a pressure differential existing over the length of the conduit 35 traversed by the air flow. As noted previously, the pressure sensor 40 is in pneumatic communication with the proximal end of the conduit 35, while the cuff 100 is in pneumatic communication with the distal end of the conduit 35. Therefore, due to the pressure losses through conduit 35 during the period of inflating the cuff 100, the pressure sensed by the pressure sensor 40 is greater than actual pressure within the inflation chamber of the cuff 100.

Figure 2:
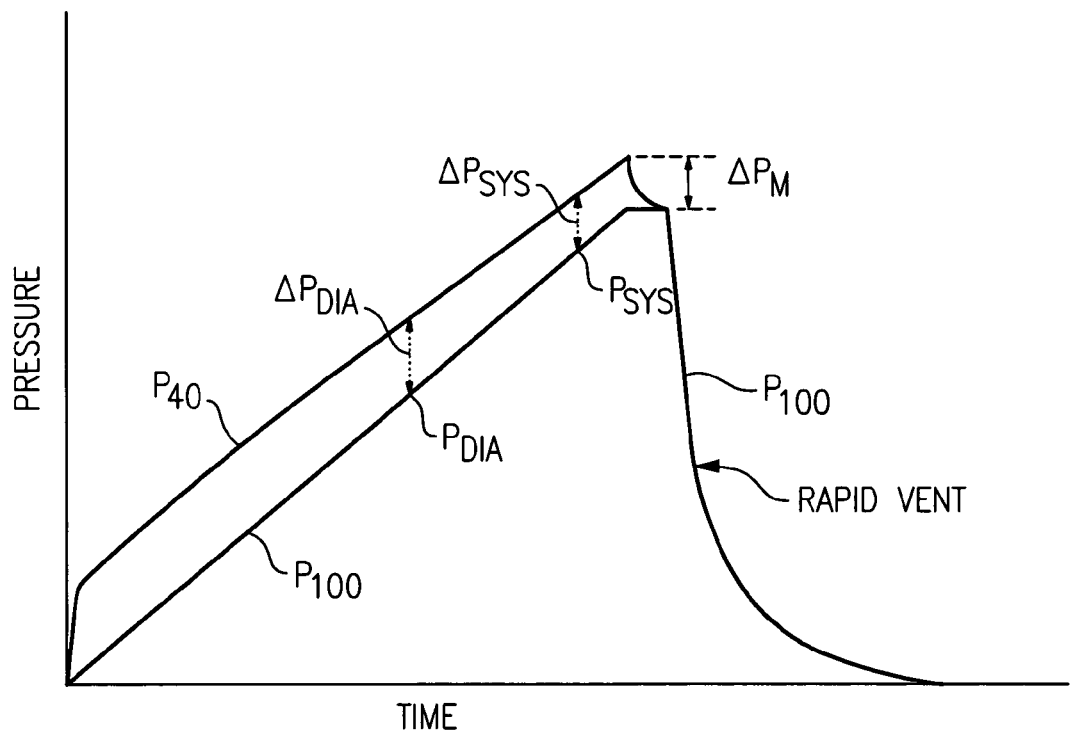
FIG. 2 is a graphical presentation illustrating an exemplary relationship of pressure over time during inflation of a blood pressure cuff via a single lumen device followed by rapid venting of the cuff.

An exemplary illustration of the relationship between the pressure sensed by the pressure sensor 40, $P_{40}$, and the actual cuff pressure, $P_{100}$, over time during the cuff inflation process is presented FIG. 2. The pressure rises relatively rapidly for a short initial period in which the flow of air through the single lumen 35 expands the inflation chamber of the cuff 100 to its maximum volume and for the period thereafter rises at a relatively linear rate. In the depicted inflation process, the flow rate of air passing through the single lumen 35 decreases during this second period of the inflation process as the pressure in the cuff 100 builds up. As noted previously, the amount of air flow passing through the lumen 35, i.e. the air flow rate, is a major determinant of the amount of pressure loss between the pressure sensor 40 and the cuff 100. Consequently, because the pressure loss varies as the air flow rate varies, the pressure differential between the pressure sensor 40 and the cuff 100 is not constant during the inflation process, but rather decreases as the pressure within the cuff 100 increases. However, if desired, the air flow rate through the single lumen 35 may be actively controlled to remain at a constant value throughout the second period of the inflation process, thereby ensuring that the pressure differential between the pressure sensor 40 and the cuff 100 also remains constant during the inflation process.

Taking the pressure differential into account, the true diastolic pressure, corresponding to the blood pressure associated with the unrestricted flow of blood through the artery, is represented by the relationship:

$$P_{DIA}=P_{40DIA}-\Delta P_{DIA}, \text{ where}$$

$P_{DIA}$ is the corrected diastolic blood pressure;
$P_{40DIA}$ is the pressure sensed at the sensor 40 when the diastolic point is reached during the cuff inflation process; and
$\Delta P_{DIA}$ is the pressure differential between the pressure sensed at the sensor 40 and the cuff pressure when the diastolic point is reached.

Similarly, the true systolic pressure, corresponding to the blood pressure associated with the cessation of the flow of blood through the artery, is represented by the relationship:

$$P_{SYS}=P_{40SYS}-\Delta P_{SYS}, \text{ where}$$

$P_{SYS}$ is the corrected systolic blood pressure;
$P_{40SYS}$ is the pressure sensed at the sensor 40 when the systolic point is reached during the cuff inflation process; and
$\Delta P_{SYS}$ is the pressure differential between the pressure sensed at the sensor 40 and the cuff pressure when the systolic point is reached.

The inflation process is terminated after the systolic point has been passed by stopping the supply of electrical power to the pump motor 60. Deflation of the cuff 100 is initiated by opening the vent valve 80, but not immediately upon termination of the inflation process. Rather, in accordance with the process of the present invention, the initiation of the cuff deflation process is delayed for a selected period of time following termination of the inflation process. During this time period, the flow of air through the conduit 35 ceases. Consequently, the pressure sensed at the pressure sensor 40, which is now in pneumatic communication with a static conduit, rapidly adjusts to match the actual pressure within the cuff. Therefore, at the end of this time delay, the cuff pressure and the pressure sensed by the pressure sensor 40 at the proximal end of the conduit 35 have equalized. The NIBP module 34 continues to monitor the sensed pressure, $P_{40}$, during this time delay as the pressure $P_{40}$ decays to match the actual cuff pressure $P_{100}$. Once the sensed pressure, $P_{40}$, stabilizes, the NIPB module 34 calculates a pressure differential, $\Delta P_M$, by subtracting the sensed pressure, $P_{40}$, at the end of the time delay from the sensed pressure, $P_{40}$, at the beginning of the time delay, which is also the sensed pressure at termination of the inflation process. Thus, $\Delta P_M$, represents the measured pressure differential between the sensed pressure at sensor 40 upon termination of the inflation process and the actual cuff pressure at cuff 100 at the termination of the inflation process.

Knowing the actual pressure differential, $\Delta P_M$, at one point of the inflation process, the actual cuff pressure at any point in the inflation process can be determined. To do so, the NIBP module 34 back calculates the pressure differentials $\Delta P_{DIA}$ and $\Delta P_{SYS}$ that existed between the sensed pressure at sensor 40 and the actual cuff pressure at the diastolic and systolic points, respectively. The NIBP module 34 then corrects the sensed pressure at sensor 40 at the diastolic and systolic points, respectively, in accord with the afore-presented relationships to calculate the true diastolic and systolic pressures. Thus, in the method of the invention, the actual cuff pressures are not directly sensed in real time at the diastolic point or the systolic point, but rather are calculated after termination of the inflation process by correcting the corresponding pressures sensed by the pressure sensor 40. In this manner, an "inflation BP" process may be utilized in connection with a single lumen blood pressure measurement apparatus.

As noted previously, the air flow rate through the single lumen 35 is the dominant determinant of the pressure loss between the pressure sensor 40 and the cuff 100. The pressure differentials $\Delta P_{DIA}$ and $\Delta P_{SYS}$ that existed between the sensed pressure at sensor 40 and the actual cuff pressure at the diastolic and systolic points, respectively, may be calculated by adjusting the measured pressure differential, $\Delta P_M$, based upon the ratio of the respective air flow rates at the diastolic, systolic and measurement points. The diastolic pressure differential may be calculated using the relationship:

$$\Delta P_{DIA}=(F_{DIA}/F_M)\Delta P_M, \text{ where}$$

$\Delta P_{DIA}$ is the pressure differential between the pressure sensed at the sensor 40 and the cuff pressure when the diastolic point is reached;
$\Delta P_M$ is the actual measured pressure differential at the sensor 40 at the measurement point;
$F_{DIA}$ is the air flow rate at the diastolic point; and
$F_M$ is the air flow rate at the measurement point.

Similarly, the systolic pressure differential may be calculated using the relationship:

$$\Delta P_{SYS}=(F_{SYS}/F_M)\Delta P_M, \text{ where}$$

$\Delta P_{SYS}$ is the pressure differential between the pressure sensed at the sensor 40 and the cuff pressure when the diastolic point is reached;

$\Delta P_M$ is the actual measured pressure differential at the sensor 40 at the measurement point;

$F_{SYS}$ is the air flow rate at the systolic point; and $F_M$ is the air flow rate at the measurement point.

The air flow rate may be based on actual flow rate measurements measured at the respective points using a conventional flow sensing device. When correcting the pressure measurements taken by the pressure 40 at the diastolic and systolic points during the inflation process, the air flow rates used in these correction relationships are the air flow rates at the diastolic and systolic points when the respective pressure measurements are taken during inflation of the cuff. The respective air flow rates may be measured at the same time as the diastolic and systolic pressures are sensed by the sensor 40, or the air flow rate may be measured continuously during the inflation process and stored in the data bank of the CPU 32, for example in a pressure versus air flow rate table, for later retrieval of the respective air flows at the diastolic and systolic points. If the flow rate change during the inflation process is not dramatic, the air flow rate may be based on flow rate estimations based on known characteristics of the cuff inflation device, e.g. the pump 50/motor 60 assembly or on empirical measurements derived from a representative apparatus 10.

In accordance with the embodiment of the invention depicted in FIG. 2, the actual pressure differential, $\Delta P_M$, is measured at the point of termination of the inflation process. In a particular embodiment of the invention, the cuff inflation process is terminated and the actual pressure differential measured promptly after the systolic blood pressure point has been surpassed. Therefore, as the actual measured pressure differential, $\Delta P_M$, is measured very near the systolic point, the air flow rate at the measurement point will be essentially equal to the air flow rate at the systolic point. Therefore, the pressure differential, $\Delta P_S$, will be essentially equal to the actual measured pressure differential, $\Delta P_M$, and for practical purposes, the systolic pressure measured at the sensor 40, $P_{40SYS}$, may be corrected using the approximation, $$P_{SYS} = P_{40SYS} - \Delta P_M.$$

Although the actual pressure differential, $\Delta P_M$, is measured in the depicted embodiment at the termination of the inflation process, it is to be understood that the actual differential, $\Delta P_M$, may be measured at other points during the inflation process and the measured diastolic and systolic pressures corrected using that measured pressure differential in accordance with the principle of the invention. The inflation process could be interrupted, for example at the diastolic point, and paused for a short period sufficient to allow the sensed pressure to decay to the cuff pressure to provide a measurement of the actual pressure differential at the diastolic point, and then restarted to further inflate the cuff 100 to a pressure above the systolic point. With the measured pressure differential, $\Delta P_M$, being the actual pressure differential measured at the diastolic point, $\Delta P_{DIA}$, the NIBP module would then calculate the pressure differential at the systolic point, $\Delta P_{SYS}$, based upon the measured pressure differential at the diastolic point corrected by the ratio of the respective air flow rates between the respective systolic and diastolic points.

As noted previously, in an embodiment of the method of the invention, the cuff inflation process may be controlled by the NIBP module 34 and/or the controller 30 to maintain a constant flow rate during cuff the inflation process to ensure that the pressure differential between the pressure sensor 40 and the cuff 100 remains constant, whereby $\Delta P_{DIA}$ and $\Delta P_{SYS}$ will both be equal to $\Delta P_M$ irrespective of whichever point in the inflation process the actual pressure differential is measured. Further, in an monitoring situation the cuff of an automated blood pressure apparatus is disposed around the limb of a subject and repeatedly inflated to measure blood pressure at selected intervals, $\Delta P_{DIA}$ and $\Delta P_{SYS}$ could be calculated once using the method of the invention and used repeatedly for correcting subsequent diastolic and systolic pressure measurements in accord with the invention.

The method of the present invention may also be used in blood pressure measurement devices capable of use in connection with both single lumen blood pressure cuffs and double lumen blood pressure cuffs. In such a device, if a dual lumen blood pressure cuff is in use, the pressure differential between the sensor pressure and the cuff pressure will be negligible and the controller of the device will not correct the sensed diastolic and systolic pressures. If a single lumen blood pressure cuff is in use, the measured pressure differential between the sensor pressure and the cuff pressure will not be negligible and the controller of the device will correct the sensed diastolic and systolic pressures in accord with the teachings of the invention.

Figure 3:
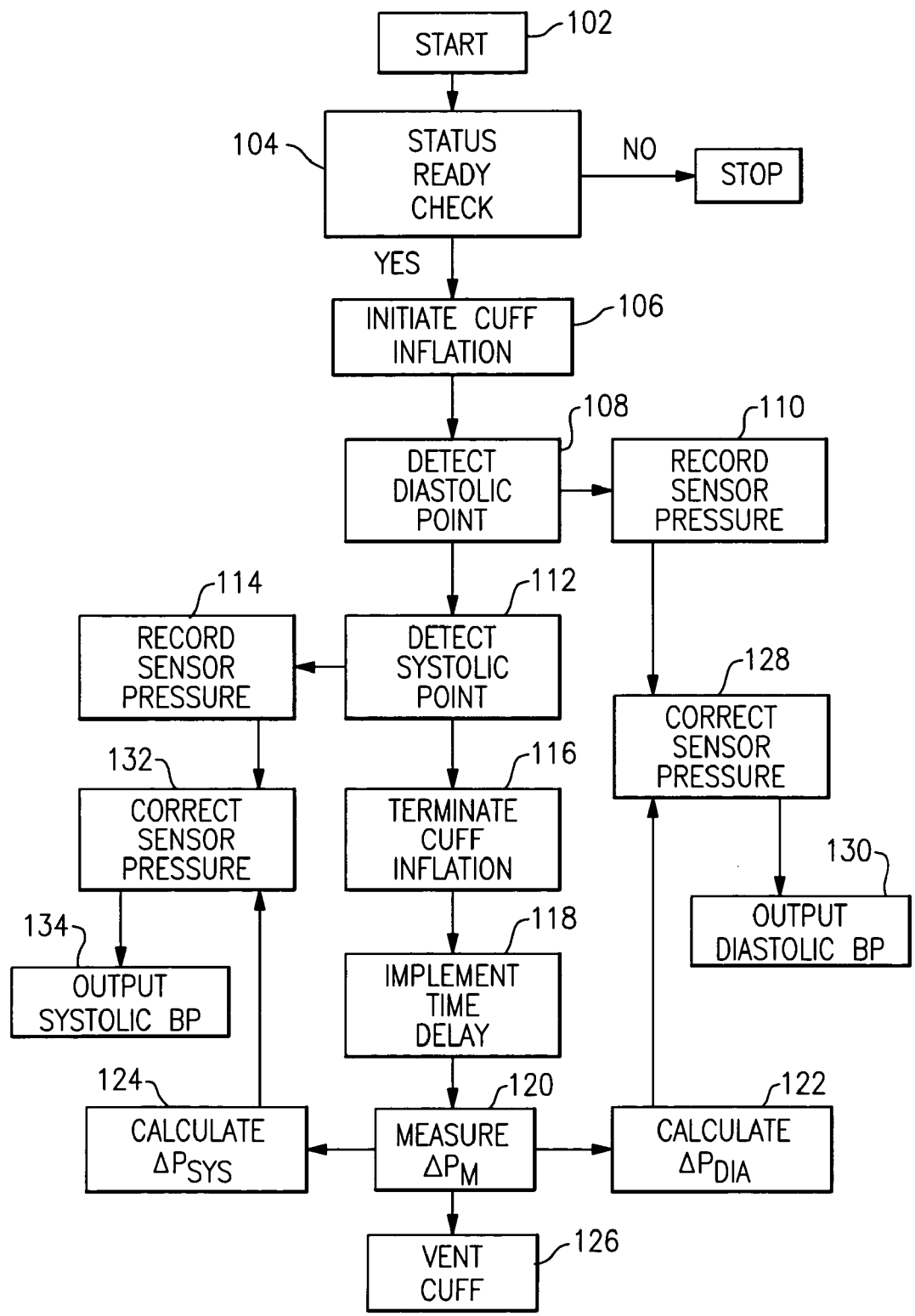
FIG. 3 is a schematic flow diagram that illustrates an exemplary embodiment of the steps in a method of determining blood pressure in accordance with the invention during cuff inflation.

An exemplary embodiment of the steps of the method of the invention for determining blood pressure from blood pressure measurements taken during the inflation process is illustrated schematically by the flow diagram depicted in FIG. 3. The process begins at step 102, labeled "Start", that represents initiation of the of the blood pressure measurement process, including at step 104 all internal initiation routines within the microprocessor 32 and the NIPB module 34 to confirm a ready status for the apparatus 10, as well as thereafter initiating at step 106, if the ready status is verified, the process of inflating the blood pressure cuff 100. If the status ready check at step 104 is negative, the process is stopped.

In order to commence a measurement of the blood pressure of an individual, the operator places an inflatable cuff 100, appropriate in size for the individual, at an appropriate location about a limb, such as an arm of the individual, presses the on/off button 21 to power up the apparatus 10, confirms that the apparatus is properly made ready, and then presses the start button 23 to initiate the cuff inflation process. Upon receipt of a start signal upon depression of the start button 23, the controller 30 opens the supply of current from the power supply 70 through line 72 to the pump motor 60 for energizing the pump motor to drive the pump 50 to pump a pressurizing fluid, most commonly air, through the tube 35 to the cuff 100, thereby initiating inflation of the cuff.

As the cuff 100 inflates, the NIPB module 34 monitors the pressure signal from the sensor electronics module to detect, using conventional oscillometric methods well known to persons having ordinary skill in the art, the diastolic point and the systolic point. However, it is to be understood that the method of the invention is not limited to any particular method for detecting the diastolic and systolic points, and other techniques known in the art, rather than oscillometric techniques, may be used for detecting the diastolic and systolic points. For example, the apparatus 10 may be equipped with a sound sensing device in operative association with the cuff 100 to listen for Korotkoff sounds for detecting the diastolic and systolic points in accord with conventional auscultatory methods well known to persons having ordinary skill in the art.

Upon detection of the diastolic point at step 108, the NIBP module 34 records the pressure then sensed by the pressure sensor 40 at step 110 and proceeds with further inflation of the cuff 100. Upon detection of the systolic point at step 112, the NIBP module 34 records the pressure then sensed by the pressure sensor 40 at step 114 and proceeds with further inflation of the cuff 100 until the pressure sensed at the sensor 40 exceeds the pressure sensed at step 114 by a preprogrammed amount. At this point, represented as step 116, the NIPB module 34 terminates the cuff inflation process and, at step 118, initiates a preprogrammed time delay. The time delay is preprogrammed to be of sufficient length following termination of the inflation process to allow the pressure at sensor 40 to decay to a stable value. Generally, one second should be sufficient. However, if desired, a longer time delay may be specified, but the time delay should be kept as short as possible so as to not prolong any patient discomfort associated with the cuff 100 being inflated to a pressure exceeding the systolic point. During the time delay, pressure sensor 40 continues to monitor the pressure at the proximal end of the conduit 35 as that pressure decays to match the actual cuff pressure 100. At the end of the time delay, at step 126, the NIBP module 34 opens the vent valve 80 to directly vent the air inflating the cuff 100 through tube 35 to atmosphere thereby deflating the cuff.

At step 120, the NIBP module 34 calculates the measured pressure differential, $\Delta P_M$, and, thereafter at steps 122 and 124 calculates, respectively, the pressure differential, $\Delta P_{DIA}$, which existed at the diastolic point, and the pressure differential, $\Delta P_{SYS}$, which existed at the systolic point, as a function of this measured pressure differential as hereinbefore discussed at paragraph [0039]. At step 128, the NIBP module 34 corrects the sensed pressure recorded at step 110 by subtracting therefrom the calculated pressure differential, $\Delta P_{DIA}$, and outputs the result at step 130 as the patient's diastolic pressure. Similarly, at step 132, the NIBP module 34 corrects the sensed pressure recorded at step 114 by subtracting therefrom the calculated pressure differential, $\Delta P_{SYS}$, and outputs the result at step 134 as the patient's systolic pressure. The microprocessor 32 may display the diastolic and systolic blood pressures on the display 20 and may store these blood pressures for later retrieval or downloading to another data storage device.

Figure 4:
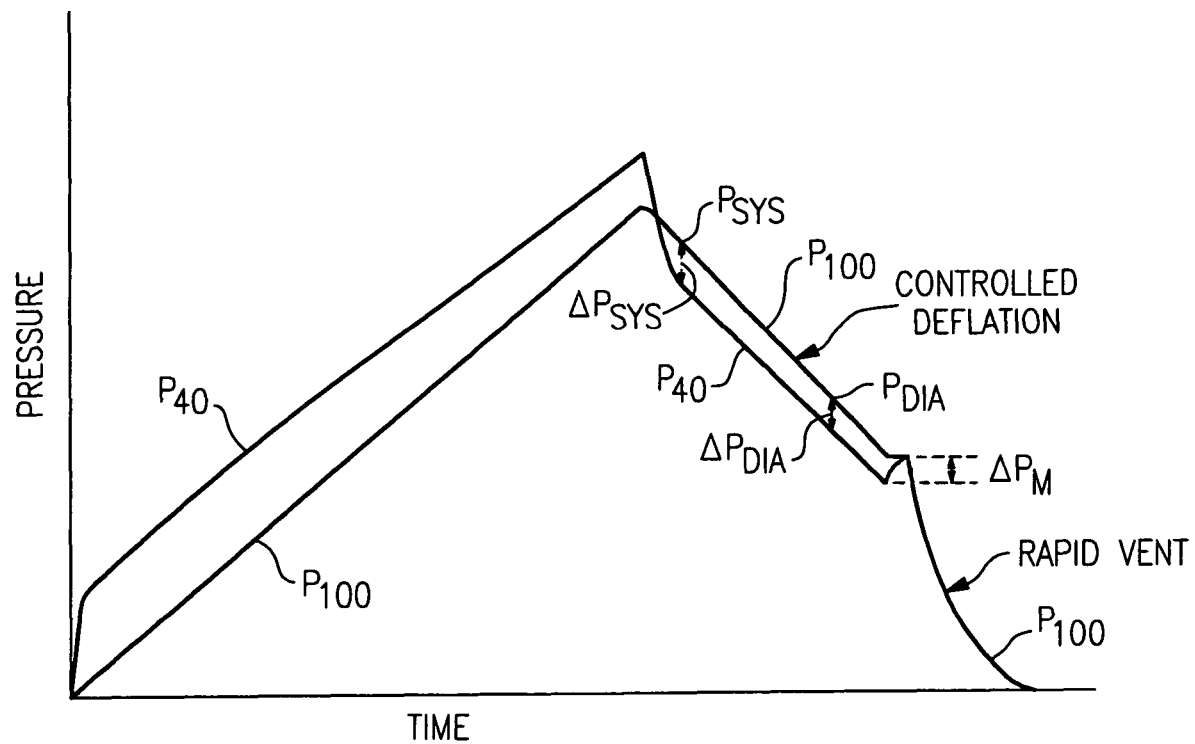
FIG. 4 is a graphical presentation illustrating an exemplary relationship of pressure over time during inflation of a blood pressure cuff via a single lumen device followed by a controlled deflation period prior to rapid venting of the cuff.

The teachings of the invention may also be implemented in connection with the measurement of blood pressure during a controlled deflation of the blood pressure cuff. Referring now to FIG. 4, there is depicted an exemplary relationship between the pressure, $P_{40}$, sensed by the pressure sensor 40 and the actual cuff pressure, $P_{100}$, over time during the inflation of the cuff 100, followed by a controlled deflation of the cuff 100 during which the systolic and diastolic pressures are sensed. In this embodiment of the invention, the inflation of the cuff 100 is terminated at a preprogrammed cuff pressure selected to be in excess of the systolic point, and then the controller 30 opens the vent valve 80 to initiate a controlled deflation of the cuff 100 until the cuff pressure has been lowered below the diastolic pressure. During the controlled deflation of the cuff 100, air exhausts from the cuff 100 through the conduit 35 and the vent valve 80 to the atmosphere. Due to the pressure loss experienced by the air flow as it exhausts through the conduit 35, the pressure, $P_{40}$, sensed at the pressure sensor 40, will be less than the cuff pressure, $P_{100}$, during the controlled deflation of the cuff 100. At a pressure below the diastolic pressure, the NIBP module 34 interrupts the deflation process and pauses the deflation process for a preprogrammed time delay sufficient for the pressure at sensor 40 to equalize with the pressure within the cuff 100. At the end of the time delay, the NIPB module 34 fully opens the vent valve 80 to cause a rapid venting of the air remaining within the cuff 100 to atmosphere.

Figure 5:
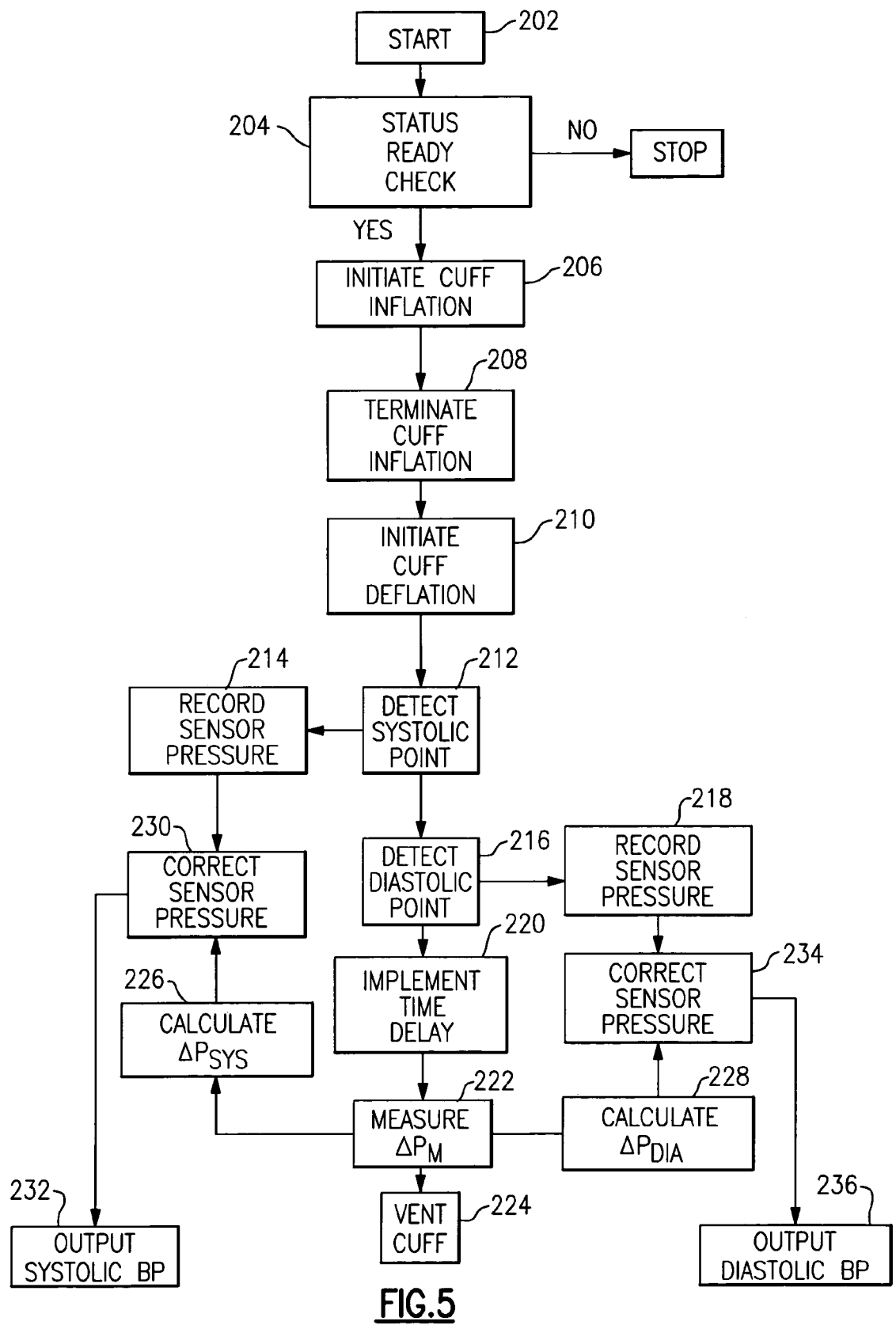
FIG. 5 is a schematic flow diagram that illustrates an exemplary embodiment of the steps in a method of determining blood pressure in accordance with the invention during cuff deflation.

Referring now to FIG. 5, an exemplary embodiment of the steps of the method of the invention for determining blood pressure from blood pressure measurements taken during the deflation process is illustrated. The process begins at step 202, labeled "Start", that represents initiation of the of the blood pressure measurement process, including at step 204 all internal initiation routines within the microprocessor 32 and the NIPB module 34 to confirm a ready status for the apparatus 10, as well as thereafter initiating at step 206, if the ready status is verified, the process of inflating the blood pressure cuff 100. If the status ready check at step 104 is negative, the process is stopped. When the blood pressure cuff 100 is inflated to a selected upper pressure level expected to be greater than the systolic pressure for the particular subject or class of subject, i.e. adult, child, infant or neonate, whose blood pressure is being measured, the NIPB module 34 terminates the cuff inflation process at step 208 and, at step 210, controlled deflation of the cuff 100 is initiated at step 210 by partially opening the vent valve 80 to directly vent the cuff 100 through tube 35 to atmosphere.

The process of the invention enables the controlled deflation process to be conducted relatively rapidly, rather than stepwise as in conventional practice, thus alleviating any potential patient discomfort. As the cuff 100 deflates the NIPB module 34 monitors the pressure signal from the sensor electronics module to detect, using conventional oscillometric methods well known to persons having ordinary skill in the art, the systolic point and the diastolic point. As noted previously, the method of the invention is not limited to any particular method for detecting the diastolic and systolic points, and other techniques known in the art, rather than oscillometric techniques, may be used for detecting the diastolic and systolic points. Upon detection of the systolic point, at step 212, as the cuff deflates, the NIBP module 34 records the pressure then sensed by the pressure sensor 40 at step 214 and proceeds with further controlled deflation of the cuff 100. Upon detection of the diastolic point at step 216, the NIBP module 34, at step 218, records the pressure then sensed by the pressure sensor 40.

After detection of the diastolic point, at step 220, the NIBP module 34 interrupts the cuff deflation process and pauses the cuff deflation process for a preprogrammed time delay is initiated. The time delay is preprogrammed to be of sufficient length following the pausing of the deflation process to allow the pressure at sensor 40 to equalize with the cuff pressure. Generally, one second should be sufficient. However, if desired, a longer time delay may be specified, but the time delay should be kept as short as possible so as to not prolong any patient discomfort. During the time delay, pressure sensor 40 continues to monitor the pressure at the proximal end of the conduit 35 as that pressure equalizes with the actual cuff pressure 100. At step 222, the NIBP module 34 determines the measured pressure differential, $\Delta P_M$, by subtracting the pressure sensed at sensor 40 at the beginning of the time delay from the pressure sensed at sensor 40 at the end of the time delay. Upon expiration of the preprogrammed time delay, the controller 30 fully opens the vent valve 80 to rapidly vent the cuff 100 to atmosphere at step 224.

Having already determined the measured pressure differential, $\Delta P_M$, the NIBP module 34 now, at steps 226 and 228 calculates, respectively, the pressure differential, $\Delta P_{SYS}$, which existed at the systolic point, and the pressure differential, $\Delta P_{DIA}$, which existed at the diastolic point, as a function of this measured pressure differential. The pressure differentials $\Delta P_{DIA}$ and $\Delta P_{SYS}$ that existed between the sensed pressure at sensor 40 and the actual cuff pressure at the diastolic and systolic points, respectively, may be calculated by adjusting the measured pressure differential, $\Delta P_M$, based upon the ratio of the respective air flow rates at the diastolic, systolic and measurement points during the controlled deflation of the cuff 100. The diastolic pressure differential may be calculated using the relationship:

$$\Delta P_{DIA} = (F_{DIA}/F_M)\Delta P_M, \text{ where}$$

$\Delta P_{DIA}$ is the pressure differential between the pressure sensed at the cuff pressure and the pressure sensed at the sensor 40 when the diastolic point is reached;

$\Delta P_M$ is the actual measured pressure differential at the sensor 40 at the measurement point;

$F_{DIA}$ is the air flow rate at the diastolic point during deflation of the cuff; and $F_M$ is the air flow rate at the measurement point.

Similarly, the systolic pressure differential may be calculated using the relationship:

$$\Delta P_{SYS} = (F_{SYS}/F_M)\Delta P_M, \text{ where}$$

$\Delta P_{SYS}$ is the pressure differential between the cuff pressure and the pressure sensed at the sensor 40 and the when the diastolic point is reached;

$\Delta P_M$ is the actual measured pressure differential at the sensor 40 at the measurement point;

$F_{SYS}$ is the air flow rate at the systolic point during deflation of the cuff; and $F_M$ is the air flow rate at the measurement point.

The air flow rate may be based on actual flow rate measurements measured at the respective points using a conventional flow sensing device during the controlled deflation of the cuff 100. When correcting the pressure measurements taken by the pressure 40 at the diastolic and systolic points during the controlled deflation process, the air flow rates used in these correction relationships are the air flow rates at the diastolic and systolic points when the respective pressure measurements are taken during deflation of the cuff. The respective air flow rates may be measured at the same time as the diastolic and systolic pressures are sensed by the sensor 40, or the air flow rate may be measured continuously during the controlled deflation process and stored in the data bank of the CPU 32, for example in a pressure versus air flow rate table, for later retrieval of the respective air flows at the diastolic and systolic points. If the flow rate change during the controlled deflation process is not dramatic, the air flow rate may be based on flow rate estimations versus pressure based on empirical measurements derived from representative cuff and conduit combinations.

At step 230, the NIPB module 34 corrects the sensed systolic pressure recorded at step 218, taking the pressure differential into account, using the relationship:

$$P_{SYS} = P_{40SYS} + \Delta P_{SYS}, \text{ where}$$

$P_{SYS}$ is the corrected systolic blood pressure;

$P_{40SYS}$ is the pressure sensed at the sensor 40 when the systolic point is reached during the cuff deflation process; and $\Delta P_{SYS}$ is the pressure differential between the cuff pressure and the pressure sensed at the sensor 40 when the systolic point is reached.

Similarly, at step 234, the NIBP module 34 corrects the sensed pressure recorded at step 222, taking the pressure differential into account, using the relationship:

$$P_{DIA} = P_{40DLA} + \Delta P_{DIA}, \text{ where}$$

$P_{DIA}$ is the corrected diastolic blood pressure;

$P_{40DIA}$ is the pressure sensed at the sensor 40 when the diastolic point is reached during the cuff deflation process; and $\Delta P_{DIA}$ is the pressure differential between the cuff pressure and the pressure sensed at the sensor 40 when the diastolic point is reached.

The NIBP module 34, at step 232, outputs the corrected systolic blood pressure as the patient's systolic blood pressure and, at step 236, outputs the corrected diastolic blood pressure as the patient's diastolic blood pressure. The microprocessor 32 may display the diastolic and systolic blood pressures on the display 20 and may store these blood pressures for later retrieval or downloading to another data storage device.

Persons possessing ordinary skill in the art will recognize that many functions and operations described herein can be implemented in hardware (for example, hard-wired logic), in software (for example, logic encoded in a program operating on a general purpose processor), and in firmware (for example, logic encoded in a non-volatile memory that is invoked for operation of a processor as required). The present invention contemplates the substitution of one implementation of hardware, software and firmware for another implementation of the equivalent functionality using a different one of hardware, software, firmware and any combination thereof. Additionally, various steps in the method of the invention to be carried out by the controller 30 may be either performed either by the CPU 32 or by the NIBP module 34, as desired.

The present invention has been particularly shown and described with reference to the preferred mode as illustrated in the drawing; it will be understood by one skilled in the art that various changes in detail may be effected therein without departing from the spirit and scope of the invention as defined by the claims.

We claim:

1. A method for determining blood pressure in an artery of a vertebrate at a diastolic point and at a systolic point using an inflatable pressure cuff disposed about a limb of the vertebrate and connected to an inflation device and a pressure sensor through a single conduit having a distal end in fluid communication with said cuff and a proximal end in fluid communication with said inflation device and in pneumatic communication with said pressure sensor, comprising the steps of:

inflating said cuff by passing a flow of an inflation fluid through said single conduit;

sensing fluid pressure within the proximal end of said conduit at the diastolic point and at the systolic point;

determining a pressure differential between said cuff and said pressure sensor at the diastolic point and a pressure differential between said cuff and said pressure sensor at the systolic point; and correcting, using a microprocessor, the sensed pressure at the diastolic point using the pressure differential at the diastolic point and correcting the sensed pressure at the systolic point for the pressure differential at the systolic point.

2. A method as recited in claim 1 wherein the step of determining a pressure differential between said cuff and said pressure sensor at the diastolic point and a pressure differential between said cuff and said pressure sensor at the systolic point comprises the steps of:

stopping the inflation of said cuff;

measuring the pressure differential between said cuff and said pressure sensor after a time delay following the stopping of the cuff inflation process; and calculating the respective pressure differentials associated with the sensed pressures at the diastolic and systolic points as a function of the measured pressure differential.

3. A method as recited in claim 2 wherein the step of measuring the pressure differential between said cuff and said pressure sensor after a time delay following the stopping of the cuff inflation process comprises the steps of:

terminating the inflation of said cuff at a cuff pressure in excess of the systolic point;

sensing the fluid pressure within the proximal end of said conduit immediately prior to termination of the cuff inflation process;

providing a time delay after termination of the cuff inflation process sufficient for fluid pressure within said cuff and within the proximal end of said conduit to equalize;

sensing the fluid pressure within the proximal end of said conduit at the end of said time delay; and subtracting the fluid pressure sensed at the end of the time delay from the fluid pressure sensed immediately prior to termination of the cuff inflation process.

4. A method as recited in claim 3 wherein the time delay is approximately one second.

5. A method as recited in claim 3 further comprising the step of venting said cuff to atmosphere after said time delay.

6. A method as recited in claim 1 further comprising the step of inflating said cuff to a cuff pressure in excess of the systolic point.

7. A method as recited in claim 1 wherein the step of sensing fluid pressure within the proximal end of said conduit at the diastolic point and at the systolic point comprises sensing fluid pressure at the diastolic point and at the systolic point during the step of inflating of said cuff.

8. A method as recited in claim 7 wherein the step of correcting the sensed pressure at the diastolic point for a pressure loss associated with the flow of an inflation fluid through said conduit comprises calculating the corrected diastolic blood pressure using the relationship:

$P_{DIA} = P_{40DIA} - \Delta P_{DIA}$, where $P_{DIA}$ is the corrected diastolic blood pressure;

$P_{40DIA}$ is the pressure sensed at the sensor 40 when the diastolic point is reached during the cuff inflation process; and $\Delta P_{DIA}$ is the pressure differential between the pressure sensed at the sensor 40 and the cuff pressure when the diastolic point is reached.

9. A method as recited in claim 7 wherein the step of correcting the sensed pressure at the systolic point for a pressure loss associated with the flow of an inflation fluid through said conduit comprises calculating the corrected systolic blood pressure using the relationship:

$P_{SYS} = P_{40SYS} - \Delta P_{SYS}$, where $P_{SYS}$ is the corrected systolic blood pressure;

$P_{40SYS}$ is the pressure sensed at the sensor 40 when the systolic point is reached during the cuff inflation process; and $\Delta P_{SYS}$ is the pressure differential between the pressure sensed at the sensor 40 and the cuff pressure when the systolic point is reached.

10. A method as recited in claim 1 further comprising the step of deflating said cuff from a cuff pressure in excess of the systolic point prior to sensing fluid pressure within the proximal end of said conduit at the diastolic and systolic points.

11. A method as recited in claim 10 wherein the step of sensing fluid pressure within the proximal end of said conduit at the diastolic point and at the systolic point comprises sensing fluid pressure at the diastolic point and at the systolic point during the step of deflating said cuff.

12. A method as recited in claim 11 wherein the step of correcting the sensed pressure at the diastolic point for a pressure loss associated with the flow of a fluid through said conduit during the step of deflating said cuff comprises calculating the corrected diastolic blood pressure using the relationship:

$P_{DIA} = P_{40DIA} + \Delta P_{DIA}$, where $P_{DIA}$ is the corrected diastolic blood pressure;

$P_{40DIA}$ is the pressure sensed at the sensor 40 when the diastolic point is reached during the step of deflating said cuff; and $\Delta P_{DIA}$ is the pressure differential between the cuff pressure and the pressure sensed at the sensor 40 when the diastolic point is reached.

13. A method as recited in claim 11 wherein the step of correcting the sensed pressure at the systolic point for a pressure loss associated with the flow of a fluid through said conduit during the step of deflating said cuff comprises calculating the corrected systolic blood pressure using the relationship:

$P_{SYS} = P_{40SYS} + \Delta P_{SYS}$, where $P_{SYS}$ is the corrected systolic blood pressure;

$P_{40SYS}$ is the pressure sensed at the sensor 40 when the systolic point is reached during the step of deflating said cuff; and $\Delta P_{SYS}$ is the pressure differential between the cuff pressure and the pressure sensed at the sensor 40 when the systolic point is reached.

14. A method as recited in claim 1 wherein the microprocessor is a CPU, an NIBP, or a microcontroller.

15. A method for determining blood pressure in an artery of a vertebrate at a diastolic point and at a systolic point using an inflatable pressure cuff disposed about a limb of the vertebrate and connected to an inflation device and a pressure sensor through a single conduit having a distal end in fluid communication with said cuff and a proximal end in fluid communication with said inflation device and in pneumatic communication with said pressure sensor, comprising the steps of: inflating said cuff by passing a flow of an inflation fluid through said single conduit;

sensing fluid pressure within the proximal end of said conduit at the diastolic point and at the systolic point during the step of inflating said cuff;

terminating the inflation of said cuff at a selected measurement point;

measuring the pressure differential existing between said pressure sensor and said cuff at termination of the cuff inflation process;

calculating the respective pressure differentials between said pressure sensor and said cuff associated with the sensed pressures at the diastolic and systolic points as a function of the measured pressure differential; and correcting, using a microprocessor, the sensed pressures at the diastolic and systolic points by subtracting the calculated diastolic pressure differential from the sensed pressure at the diastolic point and subtracting the calculated systolic pressure differential from the sensed pressure at the systolic point.

16. A method as recited in claim 15 wherein the step of measuring the pressure differential existing over said conduit at termination of the cuff inflation process comprises the steps of sensing the fluid pressure within the proximal end of said conduit immediately prior to termination of the cuff inflation process;

providing a time delay after termination of the cuff inflation process sufficient for fluid pressure within said cuff and within the proximal end of said conduit to equalize;

sensing the fluid pressure within the proximal end of said conduit at the end of said time delay; and subtracting the fluid pressure sensed at the end of the time delay from the fluid pressure sensed immediately prior to termination of the cuff inflation process thereby providing the measured pressure differential existing over said conduit at termination of the cuff inflation process.

17. A method as recited in claim 15 wherein the pressure differential associated with the sensed pressure at the diastolic point as a function of the measured pressure differential is calculated using the relationship:

$$\Delta P_{DIA} = (F_{DIA}/F_M)\Delta P_M, \text{ where}$$

$\Delta P_{DIA}$ is said pressure differential between the pressure sensed at said sensor and the pressure within said cuff when the diastolic point is reached;

$\Delta P_M$ is the actual measured pressure differential at said sensor at the measurement point;

$F_{DIA}$ is the air flow rate through said conduit at the diastolic point; and $F_M$ is the air flow rate through said conduit at the measurement point.

18. A method as recited in claim 17 further comprising the steps of measuring the air flow rate through said conduit at the diastolic point and the air flow rate through said conduit at the measurement point; and using the measured air flow rates in calculating said pressure differential at the diastolic point.

19. A method as recited in claim 17 wherein the air flow rate through said conduit at the diastolic point and the air flow rate through said conduit at the measurement point are estimated.

20. A method as recited in claim 15 wherein the pressure differential associated with the sensed pressure at the systolic point as a function of the measured pressure differential is calculated using the relationship:

$$\Delta P_{SYS} = (F_{SYS}/F_M)\Delta P_M, \text{ where}$$

$\Delta P_{SYS}$ is the pressure differential between said pressure sensor and said cuff pressure when the systolic point is reached;

$\Delta P_M$ is the actual measured pressure differential at the sensor at the measurement point;

$F_{SYS}$ is the air flow rate through said conduit at the systolic point; and $F_M$ is the air flow rate through said conduit at the measurement point.

21. A method as recited in claim 20 further comprising the steps of measuring the air flow rate through said conduit at the diastolic point and the air flow rate through said conduit at the measurement point; and using the measured air flow rates in calculating said pressure differential at the diastolic point.

22. A method as recited in claim 20 wherein the air flow rate through said conduit at the diastolic point and the air flow rate through said conduit at the measurement point are estimated.

23. A method as recited in claim 15 wherein the pressure differential associated with the sensed pressure at the systolic point as a function of the measured pressure differential is calculated using the relationship:

$$\Delta P_{SYS} = \Delta P_M, \text{ where}$$

$\Delta P_{SYS}$ is the pressure differential between said pressure sensor and said cuff pressure when the systolic point is reached;

$\Delta P_M$ is the actual measured pressure differential at the sensor at the measurement point.

24. A method as recited in claim 15 wherein the microprocessor is a CPU, an NIBP, or a microcontroller.

25. A method for determining blood pressure in an artery of a vertebrate at a diastolic point and at a systolic point using an inflatable pressure cuff disposed about a limb of the vertebrate and connected to an inflation device and a pressure sensor through a single conduit having a distal end in fluid communication with said cuff and a proximal end in fluid communication with said inflation device and in pneumatic communication with said pressure sensor, comprising the steps of:

inflating said cuff by passing a flow of an inflation fluid from said inflation device through said conduit;

terminating the inflation of said cuff at a pressure exceeding the systolic point;

deflating said cuff by venting a flow of the inflation fluid from said cuff through said conduit;

measuring the pressure differential existing between said cuff and said pressure sensor at a selected measurement point during the step of deflating said cuff;

sensing fluid pressure within the proximal end of said conduit at the diastolic point and at the systolic point during the cuff deflation step;

calculating the respective pressure differentials between said pressure sensor and said cuff associated with the sensed pressures at the diastolic and systolic points as a function of the measured pressure differential; and correcting, using a microprocessor, the sensed pressures at the diastolic and systolic points by adding the calculated diastolic pressure differential from the sensed pressure at the diastolic point and subtracting adding the calculated systolic pressure differential from the sensed pressure at the systolic point.

26. A method as recited in claim 25 wherein the step of measuring the pressure differential between said pressure sensor and said cuff at a selected measurement point during the step of deflating said cuff comprises the steps of pausing the deflation of said cuff at the selected measurement point;

sensing the fluid pressure within the proximal end of said conduit immediately prior to pausing of the cuff deflation process;

providing a time delay upon pausing of the cuff deflation process sufficient for fluid pressure within said cuff and within the proximal end of said conduit to equalize;

sensing the fluid pressure within the proximal end of said conduit at the end of said time delay; and subtracting the fluid pressure sensed immediately prior to pausing of the cuff deflation process from the fluid pressure at the end of the time delay thereby providing the measured pressure differential existing over said conduit at pausing of the cuff deflation process.

27. A method as recited in claim 25 wherein the pressure differential associated with the sensed pressure at the diastolic point as a function of the measured pressure differential is calculated using the relationship:

$$\Delta P_{DIA} = (F_{DIA}/F_M)\Delta P_M, \text{ where}$$

$\Delta P_{DIA}$ is said pressure differential between the pressure sensed at said sensor and the pressure within said cuff when the diastolic point is reached;

$\Delta P_M$ is the actual measured pressure differential at said sensor at the measurement point;

$F_{DIA}$ is the air flow rate through said conduit at the diastolic point; and FM is the air flow rate through said conduit at the measurement point.

28. A method as recited in claim 27 further comprising the steps of measuring the air flow rate through said conduit at the diastolic point and the air flow rate through said conduit at the measurement point; and using the measured air flow rates in calculating said pressure differential at the diastolic point.

29. A method as recited in claim 27 wherein the air flow rate through said conduit at the diastolic point and the air flow rate through said conduit at the measurement point are estimated.

30. A method as recited in claim 25 wherein the pressure differential associated with the sensed pressure at the systolic point as a function of the measured pressure differential is calculated using the relationship:

$$\Delta P_{SYS} = (F_{SYS}/F_M)\Delta P_M, \text{ where}$$

$\Delta P_{SYS}$ is the pressure differential between said pressure sensor and said cuff pressure when the systolic point is reached;

$\Delta P_M$ is the actual measured pressure differential at the sensor at the measurement point;

$F_{SYS}$ is the air flow rate through said conduit at the systolic point; and $F_M$ is the air flow rate through said conduit at the measurement point.

31. A method as recited in claim 30 further comprising the steps of measuring the air flow rate through said conduit at the diastolic point and the air flow rate through said conduit at the measurement point; and using the measured air flow rates in calculating said pressure differential at the diastolic point.

32. A method as recited in claim 30 wherein the air flow rate through said conduit at the diastolic point and the air flow rate through said conduit at the measurement point are estimated.

33. A method as recited in claim 25 wherein the pressure differential associated with the sensed pressure at the diastolic point as a function of the measured pressure differential is calculated using the relationship:

$$\Delta P_{DIA} = \Delta P_M, \text{ where}$$

$\Delta P_{DIA}$ is the pressure differential between said pressure sensor and said cuff pressure when the diastolic point is reached;

$\Delta P_M$ is the actual measured pressure differential at the sensor at the measurement point.

34. A method as recited in claim 25 wherein the microprocessor is a CPU, an NIBP, or a microcontroller.

* * * * *